United States Patent [19]

Axelrod

[11] Patent Number: 4,588,293

[45] Date of Patent: May 13, 1986

[54] METHOD AND APPARATUS FOR INSPECTING PHOTOMASKS TO DETECT DEFECTS

[75] Inventor: Norman N. Axelrod, New York, N.Y.

[73] Assignee: The Perkin-Elmer Corporation, Norwalk, Conn.

[21] Appl. No.: 560,679

[22] Filed: Dec. 12, 1983

[51] Int. Cl.[4] .................. G06K 9/08; G01N 21/16
[52] U.S. Cl. ..................... 356/239; 356/71
[58] Field of Search .................. 356/239, 71; 350/166

[56] References Cited

U.S. PATENT DOCUMENTS

| | | | |
|---|---|---|---|
| 3,658,420 | 4/1972 | Axelrod | 356/71 |
| 3,738,752 | 6/1973 | Heinz et al. | 356/71 |
| 3,743,423 | 7/1973 | Heinz et al. | 356/71 |
| 4,377,324 | 3/1983 | Durand et al. | 350/166 |

OTHER PUBLICATIONS

"Spatial Filtering for Detection of Signals Submerged in Noise" by Kozma et al. Apr. 1985, vol. 4, No. 4, Applied Optics, pp. 387-392.
"Computor Generated Spatial Filters for Coherent Optical Data Processing" by Lohmann et al, Apr. 1968, vol. 7, No. 4, Applied Optics, pp. 651-655.

*Primary Examiner*—John E. Kittle
*Attorney, Agent, or Firm*—Thomas P. Murphy; Edwin T. Grimes; Richard C. Wilder

[57] ABSTRACT

The present invention is directed to an improved method and apparatus for detecting defects in photomasks containing features with different arbitrary orientations, said apparatus including in one form therof a detector for detecting orientations of the features so that the optical signals from the features may be suppressed by suitable apparatus such as spatial filtering. The spatial filtering is adjusted electronically based on the determined orientation of the mask features. In one form of the invention the spatial filtering is effected by accepting photodetected signals from only a selected number of photodetectors in a photodetector array, the selection being determined by the orientation of the mask features.

40 Claims, 7 Drawing Figures ure 4,588,293

METHOD AND APPARATUS FOR INSPECTING PHOTOMASKS TO DETECT DEFECTS

FIELD OF INVENTION

This invention relates to photolithography for integrated circuits and, more particularly, to method and apparatus for inspecting photomasks to detect defects.

BACKGROUND OF INVENTION

Reference is made to my U.S. Pat. No. 3,658,420 issued Apr. 25, 1972, which describes an optical spatial filtering technique for detecting hole-type defects and excess spot defects in photomasks used in making micro-circuits. According to the patent, an approximate form factor intensity filter provides suppression of the regularly shaped mask features. Thus, for masks with features whose boundaries are along only the X-Y direction, the filter is a cross placed in the transform plane. With the rectangular features suppressed, primarily non-rectangular defect data passes so that spots as small as 0.1 mil are detected.

The present invention is directed to improvements over the methods of my earlier patent, as will become apparent as the description proceeds.

SUMMARY OF THE INVENTION

It is one object of the present invention to provide means for detecting the orientation of the mask features of the optical design. It is another object of the invention to provide means for altering the spatial filtering responsive to the detected orientation of the features so that the optical design from the mask features can be suppressed by suitable spatial filtering.

In order to accomplish the desired results, the invention provides a new and improved method and apparatus for detecting defects in photomasks containing features with different arbitrary orientations. Said apparatus includes in one form thereof detector means for detecting the orientations of the features so that the optical signals from the features may be suppressed by suitable means. One suitable means is spatial filtering. The spatial filtering is adjusted electronically based on the determined orientation of the mask features. In one form of the invention, the spatial filtering is effected by accepting photo detected signals from only a select number of photodetectors in a photodetector array, the selection being determined from the orientation of the mask features. In one form of the invention a second distinguishable defect detection beam is employed for detecting equivalent mask areas with respect to the first defect detection beam and the means for detecting defects in the mask comprises means for detecting defects in a first area of the mask using the first defect detection beam and means for detecting defects in a second equivalent area of said mask using said second defect detection beam.

There has thus been outlined rather broadly the more important features of the invention in order that the detailed decription thereof that follows may be better understood, and in order that the present contribution to the art will appreciate that the conception upon which the disclosure is based may readily be utilized as a basis for the designing of other method and apparatus for carrying out the several purposes of the invention. It is important, therefore, that the Claims be regarded as including such equivalent method and apparatus as do not depart from the spirit and scope of the invention.

Several embodiments of the invention have been chosen for purpose of illustration and description, and are shown in the accompanying drawings, forming a part of the specification.

DETAILED DESCRIPTION OF THE PREFERRED EMBODIMENTS

Figure 1:
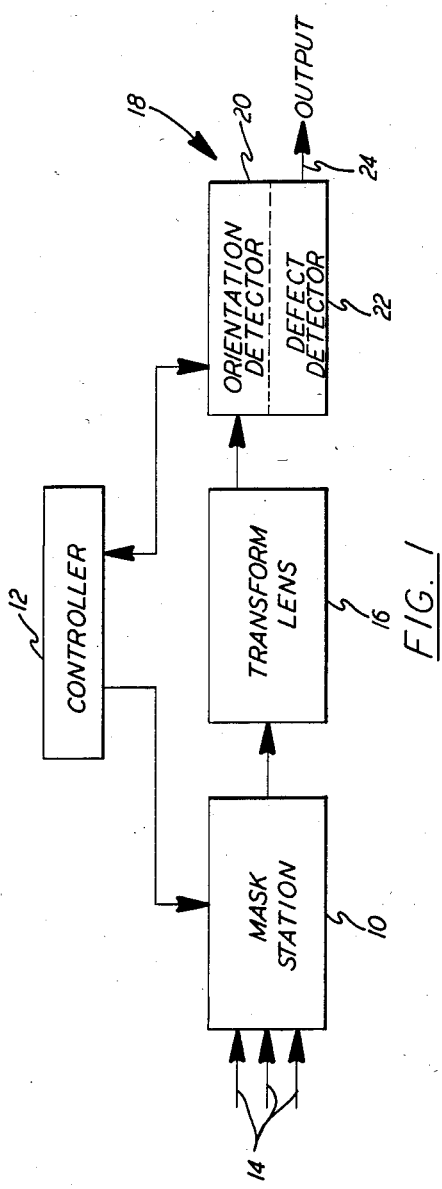
FIG. 1 is a schematic block diagram of an apparatus for inspecting masks to detect defects thereon constructed according to the concepts of the present invention.

In the embodiment of the invention illustrated in FIG. 1, apparatus for inspecting photomasks to detect defects is illustrated, which comprises a mask station 10 for mounting a mask, which is to be tested for defects. Movement of the mask into and out of position is controlled by controller means 12. Controller means 12 serves to control and coordinate the functions of the elements in the apparatus, as will be described more fully hereinafter. Source means 14 are provided for projecting radiation through the mask. This can be coherent or incoherent radiation and may or may not be in the visible range.

From the mask station the beam or beams pass to a Fourier transform lens 16, which focuses the radiation transmitted through the mask in the transform plane of the lens. In this embodiment of the invention detector means 18, under control of the controller 12, serves the multiple purposes of functioning as a spatial filter, as a demodulator or beam separator and as a detector. When functioning as a filter, the detector suppresses the regularly shaped mask features and detects mask defects from the remainder. Thus, this detector includes means 20 for detecting the orientation of the mask features using an orientation beam and outputting a corresponding signal to the controller 12, which adjusts the detector in a corresponding manner. This detector also includes means 22 for detecting defects in the mask using a defect detection beam and outputting indicia, as at 24.

Figure 5:
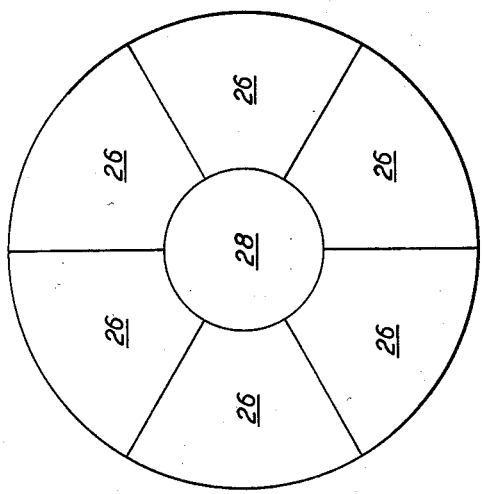
FIG. 5 is a schematic plan view of a detector array according to one form of the invention.

In one form of the invention, the mask orientation detector 20 could be in a pie-shaped configuration, as shown in FIG. 5. Thus, an array of detectors 26 appears as slices in a pie with a portion 28 near the center removed. The use of the detector array with the detectors in the form of pie slices eliminates the need for computer data acquisition and processing and permits hardwired operation with relatively simple hardware.

Figure 6:
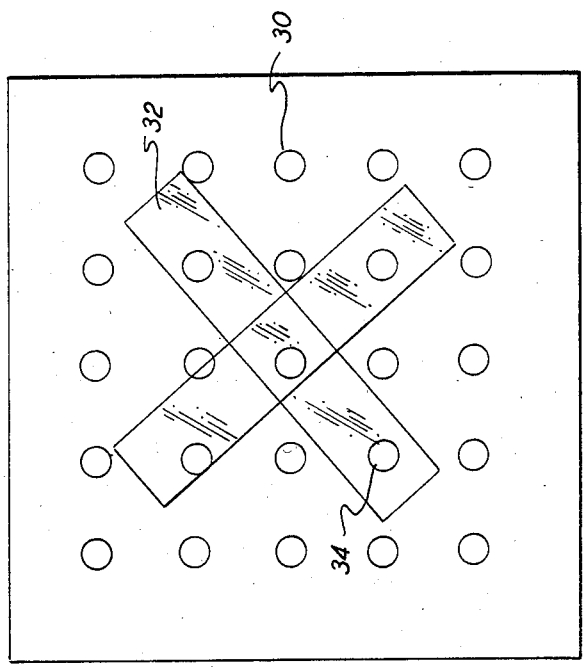
FIG. 6 is a schematic plan view of another form of the detector array according to the invention.

In another embodiment of the invention, the detector means is in the form of a rectangular array of detectors, as indicated at 30 in FIG. 6. When the beam from the mask strikes the detectors, information is signaled to the controller indicating the orientation of the mask features. The regularly shaped mask features could, for example, be in the form of a cross or a line, as indicated at 32. As a result the array of detectors is gated according to the orientation of the regularly shaped mask features. That is, the detectors 34 within the cross-shaped area are deactivated while the remaining detectors are activated, so that when the radiation from the mask is directed to the array of detectors, the activated detectors output indicia of the presence of defects in the mask.

Figure 7:
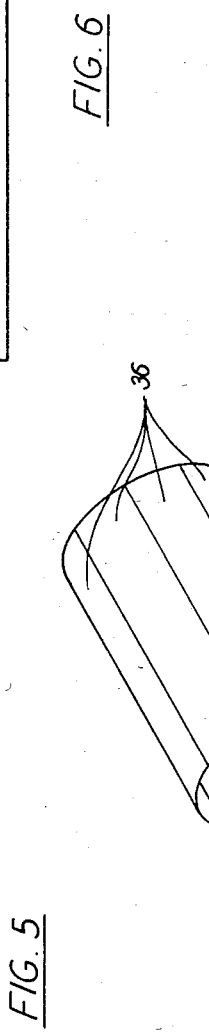
FIG. 7 is a schematic perspective view of still another form of detector array according to the invention.

FIG. 7 illustrates another desirable form of detector means for detecting the orientation of the mask features. The detector of FIG. 7 includes a plurality of strip detectors 36 disposed in a cylinder-like configuration so that the axis of the beam, indicated by an arrow 38, is coaxial with the axis of the cylinder, whereby orientation is determined by which detectors are energized.

Figure 2:
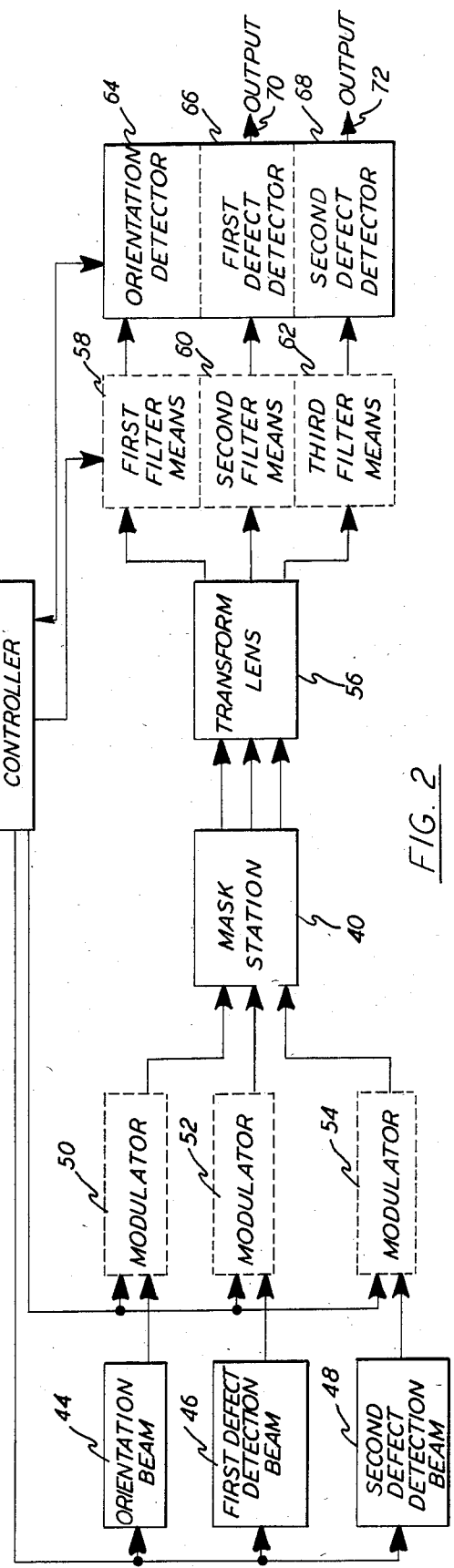
FIG. 2 is a schematic block diagram of apparatus for inspecting masks to detect defects thereon similar to FIG. 1, but showing another embodiment of the invention.

FIG. 2 shows another embodiment of the invention which includes a mask station 40 for mounting a mask, which is to be tested for defects. The mask can be moved into and out of position as controlled by controller means 42.

As pointed out in connection with the embodiment of FIG. 1, the controller serves to control and coordinate the function of the elements in the apparatus. Source means are provided for projecting radiation through the mask. As pointed out above, this can be coherent or incoherent radiation and may or may not be in the visible range. There is provided an orientation beam 44, a first defect detection beam 46 and a second defect detection beam 48, FIG. 2. These beams are passed to the mask station 40, through modulators 50, 52 and 54, respectively. Any suitable type of modulator may be employed such as, frequency modulation means, amplitude modulation means, wavelength modulation means or modulation using alternating beams, for example. These modulators are controlled by the controller 42.

Still referring to the embodiment of FIG. 2, from the mask station 40 the beam or beams pass through a Fourier transform lens 56, which focuses the radiation transmitted through the mask in the transform plane of the lens. In another form the beam or beams from the transform lens pass through filter means which could include, a first filter means 58, second filter means 60 and third filter means 62, for example. The first filter means serves to form an orientation beam, which is directed to an orientation detector 64. The second filter means serves to form a first defect detection beam, which is directed to a first defect detector 66. The third filter means serves to form a second defect detection beam, which is directed to a second defect detector 68. Any suitable form of detectors may be employed, such as, for example, those described in connection with the embodiment of FIG. 1.

In operation, the signal detected by the orientation detector 64 is sent to the controller 42, which adjusts the filter means or the defect detectors in accordance with the orientation of the mask features in response so that the first defect detector 66 outputs defect indicia as at 70 and the second defect detector 68 if employed outputs defect indicia as at 72.

In operation, in some installations the second defect detection beam 48, modulator 54, third filter means 62 and second defect detector 68 may not be employed. However, most masks contain a plurality of identical, repetitive, equivalent, circuit patterns. When these elements are employed, inspective of two or more equivalent circuit patterns can be done using one optical system. Thus, signals from two areas or more, can be distinguished by modulation of the two illuminating beams such as at different temporal frequencies, for example. In this embodiment, the defect detection means 68 followed by the filter means 62 futher separates the second defect dectection beam from the first defect detection beam and the orientation beam, so that the detector 66 detects defects in the first area of the mask using the first defect detection beam and the detector 68 detects defects in the second area of the mask using the second defect detection beam and outputting indicia thereof at 70 and 72, respectively.

Figure 3:
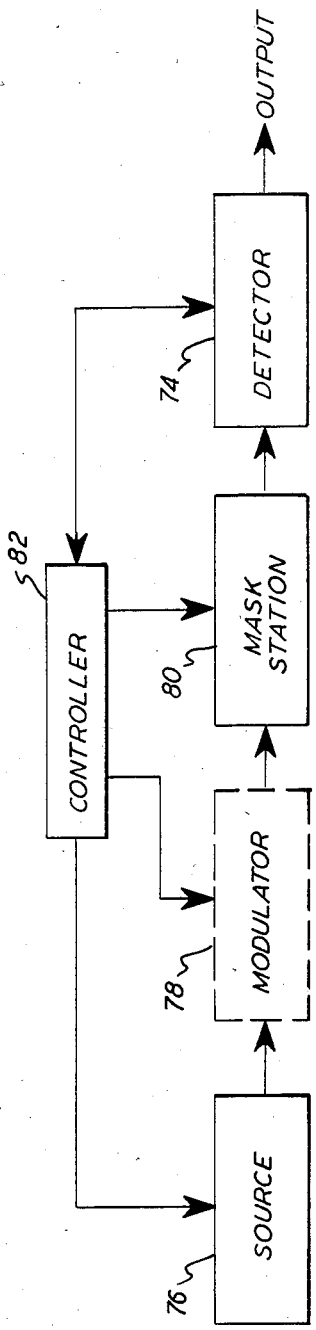
FIG. 3 is a schematic block diagram of another embodiment of the invention.

Referring next to the form of the invention illustrated in FIG. 3, this form is similar to the forms of the invention illustrated in FIGS. 1 and 2, except that the Fourier transform lens has been excluded. The apparatus detects the beam passing through the mask directly with a detector. A source 76, modulator 78, mask station 80, controller 82 may be of the same configuration and function as the corresponding elements described in connection with the embodiments of FIGS. 1 and 2. However, in this case it is essential that the beams be very small at the mask such as, for example, a diameter of less than about 1 mil of an inch each. Any suitable type of detectors may be employed such as, for example, the ones described in connection with FIGS. 5, 6 and 7.

Figure 4:
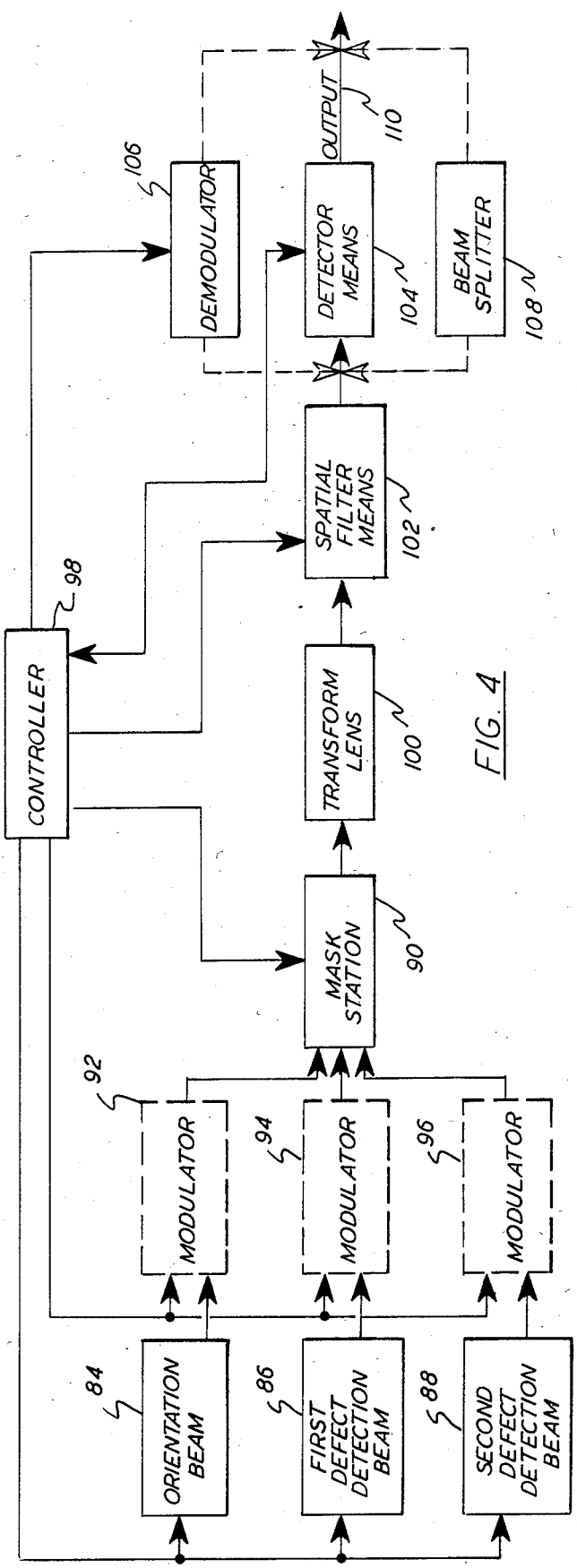
FIG. 4 is a schematic block diagram similar to FIGS. 1–3, but showing still another embodiment of the invention.

Still another embodiment of the invention is illustrated in FIG. 4. There is provided an orientation beam 84, a first defect detection beam 86 and a second defect detection beam 88. The beams pass through modulators 92, 94 and 96, respectively. Any suitable type of modulator may be employed, such as, frequency modulation means, amplitude modulation means, wave length modulation means or modulation using alternating beams, for example. These modulators as well as the beams 84, 86 and 88 are controlled by a controller 98.

From the mask station 90, the beam or beams pass to a Fourier transform lens 100, which focuses the radiation transmitted through the mask in the transform plane of the lens. In the embodiment illustrated in FIG. 4, the spatial filter means 102 are mounted substantially in said transform plane for suppressing the regularly shaped mask features and passing light tracings of defects when it has been oriented to the features of the mask. The orientation of the spatial filter 102 is controlled by controller 98. Subsequent to the spatial filter one or more of several elements may be employed, which could be employed in several possible sequences. That is, in some installations, depending on the beams passing through the mask, only detector means 104 need be employed. In this case the detector means could be of any suitable type such as one which serves the multiple purposes of functioning as a demodulator and as a detector. In other forms of the invention a demodulator 106 is mounted before the detector 104, and beamsplitter 108 is mounted before detector 104. Any suitable type of demodulator may be employed such as, for example, one which separates the orientation beam, the first detection beam and the second detection beam one from the others. The type and characteristics of the demodulator are, of course, dependent on the type and characteristics of the beams or modulators supplied. The beam splitter 108 serves to split the beam into an orientation beam, a first detection beam and a second detection beam.

The beam splitter could be dichroic whereby the beams could be split according to wavelength. In any case, signals corresponding to the orientation of the features of the mask are sent to the controller 98, which then adjusts the spatial filter means 102 to pass only the defects so that the detector means 104 outputs a signal as at 110 indicating the presence or absence of defects in the mask. Similar to the embodiment of FIG. 2, this embodiment could be either in a form employing a second detection beam and detector or in a form excluding these elements. In some installations it may be desirable to employ a large number of individual defect detection beams with corresponding detectors.

It will thus be appreciated that the present invention does indeed provide new and improved method and apparatus for inspecting masks to detect defects, which reduces the computer processing required from a detector array, and which is simpler and more accurate and faster than such apparatus employed heretofore.

Although specific embodiments have been illustrated and described, it will be obvious to those skilled in the art that various modifications may be made without departing from the spirit and scope of the invention, which is to be limited solely by the appended claims.

What is claimed is:

1. Apparatus for inspecting masks to detect defects comprising:
   a mask station for mounting a mask having features to be inspected;
   means for projecting radiation through said mask;
   means for detecting the orientations of said features;
   means for suppressing the optical signal from the features corresponding to the determined orientations of the mask features; and
   means for detecting defects in said mask and outputting indicia thereof.

2. Apparatus for inspecting masks to detect defects according to claim 1 wherein said means for detecting the orientations of the mask features comprises a plurality of strip detectors disposed in a cylinder-like configuration so that the axis of the beam is along the axis of the cylinder, whereby orientation is determined by which detectors are energized.

3. Apparatus for inspecting masks to detect defects according to claim 1, wherein the projecting radiation is in the form of a beam having a diameter of less than about 1 mil of an inch.

4. Apparatus for inspecting masks to detect defects according to claim 1 wherein said means for detecting the orientation of the mask features comprises a substantially circular configuration of individual detectors disposed around the optical axis in a pie-like array with the portion near the center removed.

5. Apparatus for inspecting masks to detect defects according to claim 1 wherein said means for detecting the orientation of the mask features comprises a substantially rectangular array of detectors.

6. Apparatus for inspecting masks to detect defects according to claim 1 wherein said means for projecting radiation comprises a first source for projecting an orientation beam to said mask station and a second separate source for projecting a defect detection beam to said mask station.

7. Apparatus for inspecting masks to detect defects according to claim 6 further comprising means for discriminating the signals from the orientation beam and from the defect detection beam.

8. Apparatus for inspecting masks to detect defects according to claim 7 wherein said means for discriminating signals from the orientation beam and from the defect detection beam comprises a beam splitter.

9. Apparatus for inspecting masks to detect defects according to claim 6 wherein said orientation beam and said defect detection beam have different optical wavelengths.

10. Apparatus for inspecting masks to detect defects according to claim 6 wherein said orientation beam and said defect detection beam have different modulation frequencies.

11. Apparatus for inspecting masks to detect defects according to claim 6, wherein the diameters of said beams are less than about 1 mil of an inch respectively, and wherein said means for detecting the orientations and said means for detecting defects comprises an array of detectors mounted adjacent said mask, and means for gating said array of detectors according to the orientation of the regularly shaped mask features, and means for detecting defects in said mask using said gated array of detectors.

12. Apparatus for inspecting masks to detect defects comprising:
    a mask station for mounting a mask having features to be inspected;
    source means for projecting radiation through said mask;
    means for forming an orientation beam;
    means for forming a defect detection beam;
    a controller;
    means for detecting the orientation of the mask features and outputting a corresponding signal to said controller using said orientation beam; and
    means for detecting defects in said mask and outputting indicia thereof using said defect detection beam, said controller controlling said means for detecting defects corresponding to the orientation of the mask features.

13. Apparatus for inspecting masks to detect defects according to claim 12 wherein said means for detecting the orientation of the mask features comprises a plurality of strip detectors disposed in a cylinder-like configuration so that the axis of the beam is along the axis of the cylinder, whereby orientation is determined by which detectors are energized.

14. Apparatus for inspecting masks to detect defects according to claim 12, wherein the diameters of said beams are less than about 1 mil of an inch, respectively.

15. Apparatus for inspecting masks to detect defects according to claim 12 wherein said means for detecting the orientation of the mask features comprises a substantially circular configuration of individual detectors disposed around the optical axis in a pie-like array with the portion near the center removed.

16. Apparatus for inspecting masks to detect defects according to claim 12 wherein said means for detecting the orientation of the mask features comprises a substantially rectangular array of detectors.

17. Apparatus for inspecting masks to detect defects according to claim 12 wherein said source means comprises a first source for projecting the orientation beam to said mask station and a second separate source for projecting the defect detection beam to said mask station.

18. Apparatus for inspecting masks to detect defects according to claim 12 further comprising means for discriminating the signals from the orientation beam and from the defect detection beam.

19. Apparatus for inspecting masks to detect defects according to claim 18 wherein said means for discriminating signals from the orientation beam and from the defect detection beam comprises a beam splitter.

20. Apparatus for inspecting masks to detect defects according to claim 12 wherein said orientation beam and said defect detection beam have different optical wavelengths.

21. Apparatus for inspecting masks to detect defects according to claim 12 wherein said orientation beam and said defect detection beam have different modulation frequencies.

22. Apparatus for inspecting masks to detect defects according to claim 12, wherein the diameters of said beams are less than about 1 mil of an inch respectively, and wherein said means for detecting the orientation and said means for detecting defects comprise an array of detectors mounted adjacent said mask, and means for gating said array of detectors according to the orientation of the regularly shaped mask features, and means for detecting defects in said mask using said gated array of detectors.

23. Apparatus for inspecting masks to detect defects comrising:
a mask station for mounting a mask having features to be inspected;
source means for projecting radiation through said mask;
means for forming an orientation beam;
means for forming a defect detection beam;
a controller;
a transform lens, mounted in the path of said radiation, for focusing the radiation transmitted through said mask in the transform plane of said mask;
means for detecting the orientation of the mask features using said orientation beam and outputting a corresponding signal to said controller; and
means for detecting defects in said mask using said defect detection beam and outputting indicia thereof, said controller controlling said means for detecting defects corresponding to the orientation of the mask features.

24. Apparatus for inspecting masks to detect defects acording to claim 23 wherein said means for detecting the orientation of the mask features comprises a plurality of strip detectors disposed in a cylinder-like configuration so that the axis of the beam is along the axis of the cylinder, whereby orientation is determined by which detectors are energized.

25. Apparatus for inspecting masks to detect defects according to claim 23, wherein the diameters of said beams are less than about 1 mil of an inch, respectively.

26. Apparatus for inspecting masks to detect defects according to claim 23 wherein said means for detecting the orientation of the mask features comprises a substantially circular configuration of individual detectors disposed around the optical axis in a pie-like array with the portion near the center removed.

27. Apparatus for inspecting masks to detect defects according to claim 23 wherein said means for detecting the orientation of the mask features comprises a substantially rectangular array of detectors.

28. Apparatus for inspecting masks to detect defects according to claim 23 wherein said source means comprises a first source for projecting the orientation beam to said mask station and a second separate source for projecting the defect detection beam to said mask station.

29. Apparatus for inspecting masks to detect defects according to claim 23 further comprising means for discriminating the signals from the orientation beam and from the defect detection beam.

30. Apparatus for inspecting masks to detect defects according to claim 29 wherein said means for discriminating signals from the orientation beam and from the defect detection beam comprises a beam-splitter.

31. Apparatus for inspecting masks to detect defects according to claim 23 wherein said orientation beam and said defect detection beam have different optical wavelengths.

32. Apparatus for inspecting masks to detect defects according to claim 23 wherein said orientation beam and said defect detection beam have different modulation frequencies.

33. Apparatus for inspecting masks to detect defects according to claim 23, wherein the diameters of said beams are less than about 1 mil of an inch respectively, and wherein said means for detecting the orientation and said means for detecting defects comprises an array of detectors mounted adjacent said mask, means for gating said array of detectors according to the orientation of the regularly shaped mask features, and means for detecting defects in said mask using said gated array of detectors.

34. Apparatus for inspecting masks to detect defects according to claim 23 further comprising a second distinguishable defect detection beam for detecting equivalent mask areas with respect to the first defect detection beam, and wherein said means for detecting defects in said mask comprises means for detecting defects in a first area of said mask using said first defect detection beam and means for detecting defects in a second equivalent area of said mask using said second defect detection beam.

35. Apparatus for inspecting masks to detect defects comprising:
an optical system having a Fourier transform plane;
means for mounting a mask having regularly shaped mask features in said optical system;
means mounted substantially in said transform plane for suppressing the regularly shaped mask features and passing light tracings of defects;
means for detecting the orientation of the regularly shaped mask features;
means for adjusting the means for suppressing the regularly shaped masked features based on the determined orientation of the mask features; and
means for detecting said passed light to produce an output indicative of the presence of defects.

36. Apparatus for inspecting masks to detect defects comprising:
an optical system having a Fourier transform plane;
means for mounting a mask having regularly shaped mask features in said optical system;
an approximate form factor intensity spatial filter mounted substantially in said transform plane for suppressing the regularly shaped masked features and passing light tracings of defects;
means for detecting the orientation of the mask features;
means for adjusting said spatial filter based on the determined orientation of the mask features;

means for detecting said passed light to produce an output; and means for utilizing said output to generate indicia of defects in said mask.

37. Method of detecting defects in a photomask containing circuit elements, comprising the steps of:
mounting a mask having features to be inspected in a mask station;
projecting radiation through said mask;
detecting the orientations of said features;
suppressing the optical signal from the features corresponding to the determined orientation of the mask features; and
detecting defects in said mask and outputting indicia thereof.

38. Method of detecting defects in a photomask containing circuit elements, comprising the steps of:
mounting a mask having features to be inspected in a mask station;
projecting radiation through said mask;
forming an orientation beam;
forming a defect detection beam;
detecting the orientation of the mask features and outputting a corresponding signal to a controller using said orientation beam; and
detecting defects in said mask and outputting indicia thereof using said defect detection beam which is controlled by said controller corresponding to the orientation of the mask features.

39. Method of detecting defects in a photomask containing circuit elements, comprising the steps of:
mounting a mask having features to be inspected in a mask station;
projecting radiation through said mask;
forming an orientation beam;
forming a defect detection beam;
mounting a transform lens in the path of said radiation for focusing the radiation transmitted through said mask in the transform plane of said mask;
detecting the orientation of the mask features using said orientation beam and outputting a corresponding signal to a controller; and
detecting defects in said mask using said defect detection beam controlled by said controller corresponding to the orientation of the mask features and outputting indicia thereof.

40. Method of detecting defects in a photomask containing circuit elements, comprising the steps of:
mounting a mask having regularly shaped mask features in a optical system having a Fourier transform plane;
mounting an approximate form factor intensity spatial filter substantially in said transform plane for suppressing the regularly shaped masked features and passing light tracings of defects;
detecting the orientation of the mask features;
adjusting said spatial filter based on the determined orientation of the mask features;
detecting said passed light to produce an output; and
utilizing said output to generate indicia of defects in said mask.

* * * * *